United States Patent [19]

Carpel

[11] 4,122,848

[45] Oct. 31, 1978

[54] SURGICAL DRAPE SUPPORT

[76] Inventor: Emmett F. Carpel, 2683 E. Lake of the Isles Blvd., Minneapolis, Minn. 55408

[21] Appl. No.: 791,928

[22] Filed: Apr. 28, 1977

[51] Int. Cl.$^2$ .............................................. A61B 19/06
[52] U.S. Cl. .................................................. 128/132 D
[58] Field of Search ...... 128/132 R, 132 D, DIG. 26, 128/185, 205, 139; 5/334 B, 321; 269/328; 2/9, 206

[56] References Cited

U.S. PATENT DOCUMENTS

| | | | |
|---|---|---|---|
| 1,048,191 | 12/1912 | Maurice | 2/206 |
| 1,238,154 | 8/1917 | Kemp | 2/206 |
| 2,290,437 | 7/1942 | Kilgore | 128/205 |
| 2,774,970 | 12/1956 | DuBois | 2/9 |
| 3,347,544 | 10/1967 | Uffenorde | 269/328 |
| 3,403,677 | 10/1968 | Struve | 128/205 |

Primary Examiner—Lawrence W. Trapp
Attorney, Agent, or Firm—Burd, Braddock & Bartz

[57] ABSTRACT

A support for a surgical drape to support the drape in the vicinity of a surgical patent's face and elevated above the nose of the patient to permit unimpeded breathing by the patient during a surgical process, and, in particular, during an ophthalmologic procedure. The support includes a base securable to the nose, and a holder extended from the base to a position above the nose of the patient and over the facial area where air is normally drawn through the nose and mouth for breathing.

15 Claims, 5 Drawing Figures

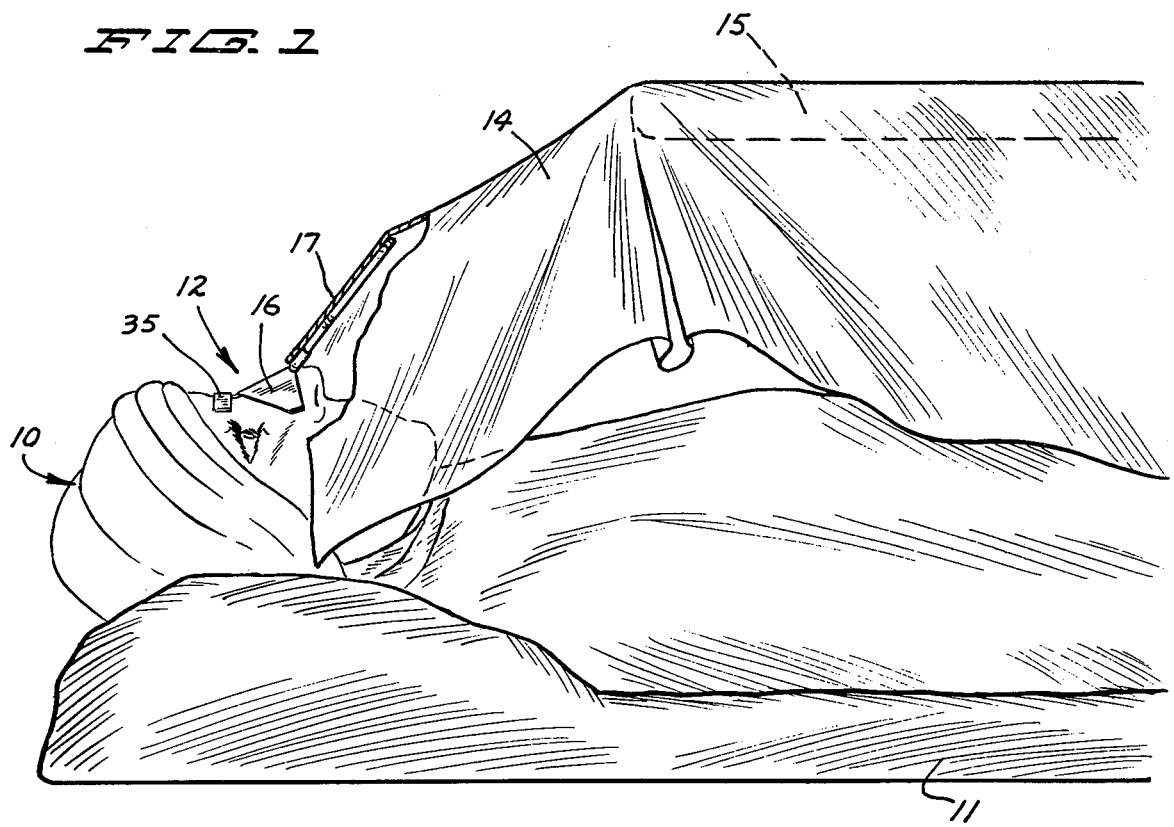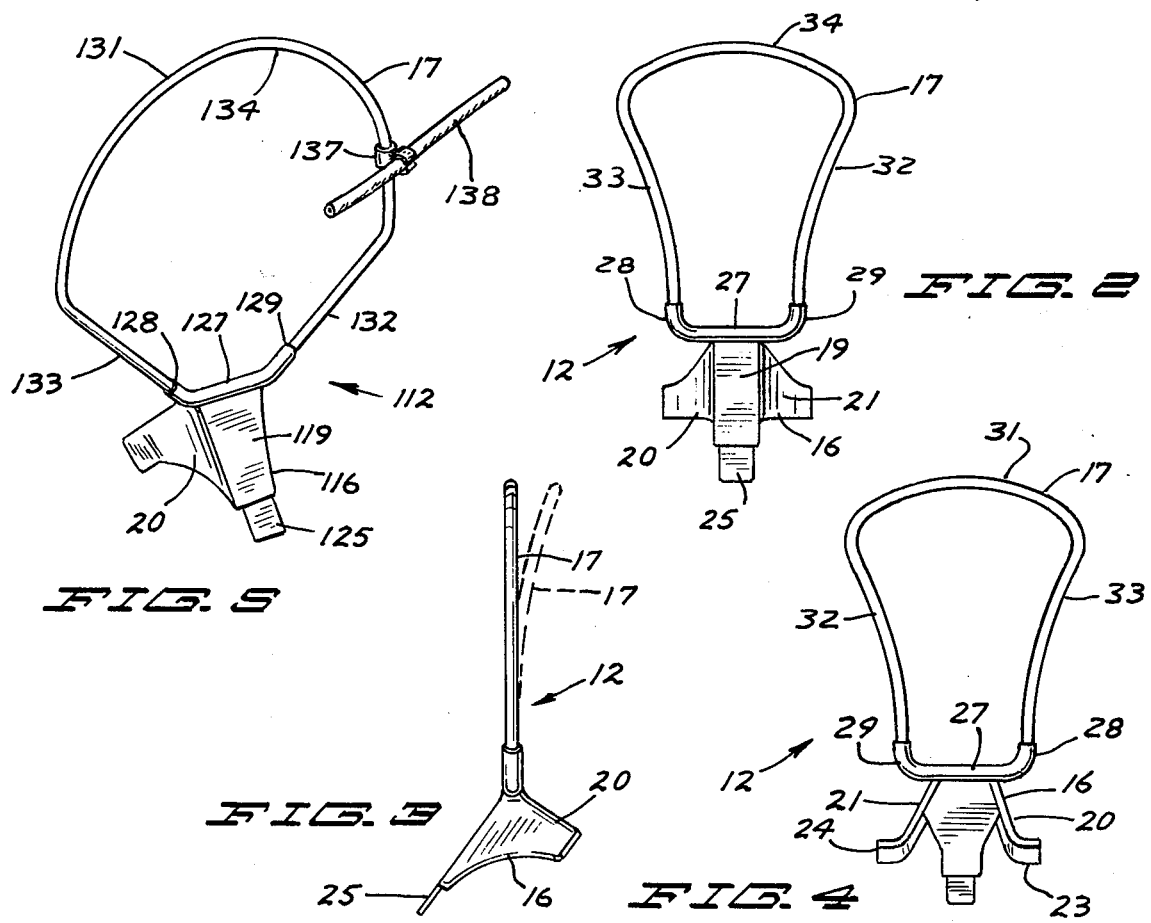

SURGICAL DRAPE SUPPORT

BACKGROUND OF INVENTION

During surgical procedures, it is standard practice for sanitary reasons to drape the patient with a sheet or surgical drape exposing only the surgical field. In the case of eye surgery, this means that the drape extends over the patient's face and thus the nose, mouth and other eye. The patient, under a local anesthetic, is apt to experience a feeling of claustrophobia, and feel anxiety about and actually experience difficulty in free breathing. The nature of surgical drape material can be such that it is prone to cling and closely conform to the body parts thus to enhance the unpleasant sensations encountered when draped over a patient's face.

Various devices have been proposed for spacing the surgical drape above the patient's face. For example, see U.S. Pat. No. 3,530,515 to Jacoby issued Sept. 29, 1970, which shows a device requiring special equipment on the operating table for attachment thereto. U.S. Pat. No. 3,347,544 to Uffenorde, issued Oct. 17, 1967 also shows a device for elevating the surgical drape above the face of the patient during eye surgery.

SUMMARY OF THE INVENTION

The invention relates to a support for holding a surgical drape spaced from the nose and mouth of the surgical patient to permit uninhibited breathing and deter any claustrophobic sensation otherwise encountered when the drape is nearly flush to the patient's face. The support includes a base which is fixable to a portion of the patient's head or face, preferably in spanning or bridging relationship to the upper part of the nose. The base can be malleable so to be made to conform to the face portion of a particular patient. A holder extends from the base outward from the patient's face to a location over the nose and mouth of the patient when the patient is in a supine position on an operating table. The holder keeps the surgical drape spaced from the nose and mouth of the patient. The support is compact so to be easily stored with other instruments of eye surgery. It is also readily sterilizable. Use of the support requires no special operating table equipment.

IN THE DRAWINGS

FIG. 1 is a fragmentary side elevational view partly in section showing the surgical drape support of the invention in use on a patient in an operating theatre;

FIG. 2 is a front elevational view of the surgical drape holder shown in FIG. 1;

FIG. 3 is a side elevational view of the surgical drape holder shown in FIG. 1;

FIG. 4 is a rear elevational view of the surgical drape support shown in FIG. 1; and FIG. 5 is a perspective view of a modification of a surgical drape holder of the invention.

DESCRIPTION OF PREFERED EMBODIMENTS

Referring to the drawings, there is shown in FIG. 1 an eye surgery patient 10 in a supine position on an operating table 11 prepatory to eye surgery or other ophthalmologic procedure. A surgical drape support, indicated generally at 12, is fitted to the face of the patient 10 and supports a surgical drape 14 in the vicinity of the nose and mouth of patient 10. Surgical drape 14 is disposed to cover all of the face of patient 10 except the eye upon which surgery is to be performed. Drape 14 extends from the face of the patient 10 to an implement table 15 which can hold the various instruments used by the surgeon. Drape support 12 supports the drape 14 above the nose and mouth of patient 10 sufficiently that the patient can breathe freely and uninhibited, and not experience a sensation of clostrophobia.

Referring to FIGS. 2–4, surgical drape support 12 includes a bracket or base 16 and a holder 17 secured to and extending from the base 16. Base 16 has a face or broad front section 19 and legs 20, 21 symetrically extended from the front section 19. Legs 20, 21 diverge slightly as they extend away from the front section 19 and together with the front section form a generally U-shaped pocket. Outwardly turned feet 23, 24 extend away from the ends of the legs 20, 21 respectively, as best shown in FIG. 4.

Base 16 is shaped generally to conform to the upper portion of the nose of a surgical patient and can be formed of a malleable metal or other material so as to be easily bent or shaped to better conform to the patient's nose. As shown, base 16 can be covered with a rubber or plastic coating or jacket for patient comfort. A lip 25 is constituted as a longitudinal extension of front section 19 and is provided for securing base 16 to the patient's face as with a piece of surgical tape.

At the end of front section 19 opposite lip 25 is an elongate, transversely oriented tubular shoulder 27 having forwardly extended open ends or sockets 28, 29 for receipt of portions of holder 17. Holder 17 is comprised of coplanar loop 31 of rod shaped material of metal, wire, or plastic or the like.

Loop 31 is somewhat rectangularly shaped, having arms 32, 33 extended generally forward and slightly outward, to a generally arcuate mid portion 34. The inner end portions of arms 32, 33 are fixed in the end sockets 28, 29 of shoulder 27. As shown in phantom in FIG. 3, loop 31 can be formed of a malleable material so as to be bent as needed, for example, to allow added clearance for micro-surgical instrumentation. In addition, end sockets 28, 29 of shoulder 27 can be of bendable material to permit alteration of the shape of loop 31 as needed or desired.

In use of drape support 12 as shown in FIG. 1, base 16 is placed over the upper portion of the nose of the patient with the legs 20, 21 straddling the nose and the front section 19 resting on the bridge of the nose. Lip 25 extends toward the forehead. The legs 20, 21 can be bent relative to front section 19 to optimize the fit. Feet 23, 24 rest on the cheeks of the patient adjacent the nose. The load of the support and drape is thus distributed about the nose proximity and not concentrated at any single location. A piece of surgical tape 35 is affixed to lip 25 of base 16 and a portion of the patient's forehead to assist maintaining the base 16 in place.

With base 16 so positioned, loop 31 of holder 17 extends up over the nose and mouth of patient 10 over that area from where the patient normally draws breath. Surgical drape 14 is draped over the loop 31 where it is kept spaced from the patient's breathing area.

Surgical drape support 12 is compact, allowing room around the operating area for needed micro-surgical instrumentation, without interfering with the surgeon or any assistants. The support is adaptable to any type of operating environment as it relies upon the patient for support rather than specialized operating table equipment. The device can be readily sterilized and the compact size permits it to be stored with the other eye surgery instruments.

There is shown in FIG. 5 a modified surgical drape support 112 having a similar base 116 with a front section 119 and a pair of symetrical legs only one of which is shown at 120. A longitudinal lip 125 is provided to assist in securing the base 116 to the patient's face. A transversely orientated shoulder 121 is fixed to base 116 and has angularly outwardly extended open ends or sockets 128 and 129. A holder 131 is formed of rod-like material and has a semi-circular mid portion 134. Straight arms 132, 133 extend from the semi-circular mid portion 134 to the open end sockets 128, 129 of transverse shoulder 127. Holder 131 of surgical drape support 112 is similar to the holder 31 of surgical drape support 12 except that a broader support area is provided for those instances when such is needed or required. A clip 137 is secured to the holder 131. Clip 137 is adapted to hold a portion of an air or oxygen hose, indicated at 138, so that the end is in proximity to the breathing area of the patient to provide additional air or oxygen when needed.

While there has been shown and described certain embodiments of the invention, it will be apparant to those skilled in the art that deviations from the embodiments shown can be made without departing from the scope and spirit of the invention.

The embodiments of the invention in which an exclusive property or privilege is claimed are defined as follows:

1. A surgical drape support to space a surgical drape from the breathing area of a supine surgical patient during an ophthalmologic surgical procedure, comprising:
   base means mountable to a portion of the face of the surgical patient;
   holder means secured to the base means and extended therefrom to a location above the nose and mouth of the patient over the breathing area of the patient and away from the eyes of the patient when the base means is mounted on the face of the patient, to support a surgical drape above the breathing area of the patient; and a surgical drape supported on the holder means over the breathing area of the patient to permit unimpeded breathing of the patient during an ophthalmologic surgical procedure.

2. The surgical drape support of claim 1 wherein: said base means is shaped to be mountable on the upper nose portion of the surgical patient.

3. The surgical drape support of claim 2 wherein: said base means has a front section to span the upper nose portion of the patient, and a pair of symetrical legs, one each of said legs extending from either side of the front section to be in straddling relationship to the patient's nose.

4. The surgical support in claim 3 including: a lip extending from said front section of the base means toward the patient's forehead when said legs are in straddling relationship to the patient's nose, said lip adapted for receipt of a piece of surgical tape to secure the base means to the head of the patient.

5. The surgical drape support of claim 4 including: an outwardly directed foot at the end of each leg to bear upon the patient's face and assist in support of the base means, holder means, and surgical drape.

6. The surgical drape support of claim 5 wherein: said holder means consists of a coplanar loop or rod-like material.

7. A surgical drape support to space a surgical drape from the breathing area of a supine surgical patient during a surgical procedure, comprising:
   base means shaped to be mountable on the upper nose portion of the surgical patient;
   holder means consisting of a coplanar loop of rod-like material secured to the base means and extended therefrom to a location above the breathing area of the patient when the base means is mounted on the nose of the patient, to support a surgical drape above the breathing area of the patient;
   said base means having a front section to span the upper nose portion of the patient, a pair of symmetrical legs, one each of said legs extending from either side of the front section to be in straddling relationship to the patient's nose, and an outwardly directed foot at the end of each leg to bear upon the patient's face and assist in support of the base means, holder means and surgical drape;
   said base means also including a transverse shoulder having open end sockets, said holder loop having an arcuate mid-section and generally straight ends, said ends being secured in the sockets of the transverse shoulder of the base means.

8. The surgical drape support of claim 7 wherein: said base is constituted of a malleable material able to be shaped to closely fit the patient's face portion.

9. The surgical drape support of claim 8 wherein: said base is formed of a malleable metal and has a coating of flexible material.

10. A surgical drape support to space a surgical drape from the breathing area of a supine surgical patient during a surgical procedure, comprising:
    base means mountable to a portion of the face of the surgical patient;
    holder means secured to the base means and extended therefrom to a location above the breathing area of the patient when the base means is mounted on the face of the patient, to support a surgical drape above the breathing area of the patient, said holder means consisting of a coplanar loop of malleable rod-like material.

11. The surgical drape support of claim 10 wherein: said base means is shaped to be secured to the nose of the patient and includes a transverse shoulder with open end sockets, said holder loop having an arcuate mid portion and straight ends secured in the end sockets of the shoulder of the base means.

12. A surgical drape support to space a surgical drape from the breathing area of a supine surgical patient during an ophthalmologic surgical procedure, comprising:
    a base securable to the upper nose portion of a patient in straddling relationship relative to the nose;
    a holder secured to the base and extending therefrom to a location over the nose and mouth of the patient to be over the breathing area of the patient proximate the nose and mouth of the patient and away from the eyes of the patient to space a surgical drape from the breathing area of the patient when the base is secured to the upper nose portion of the patient and permit access to an eye of the patient for a surgical procedure; and
    a surgical drape supported on the holder over the nose and mouth of the patient to permit unimpeded breathing of the patient during an ophthalmologic surgical procedure.

13. The surgical drape support of claim 12 including: a clip connected to said holder to hold a portion of an air hose.

14. A surgical drape support to space a surgical drape from the breathing area of a supine surgical patient during a surgical procedure, comprising:

a base securable to the upper nose portion of a patient in straddling relationship relative to the nose;

a holder comprised of a wire loop secured to the base and extending therefrom to a location over the breathing area of the patient proximate the nose and mouth of the patient to space a surgical drape from the breathing area of the patient when the base is secured to the upper nose portion of the patient.

15. The surgical drape support of claim 14 wherein: said base is formed of a malleable material and has a front section for spanning the upper portion of the nose, a pair of legs, one each of said legs extending from either side of the front section in straddling relationship to the nose, and a lip extending from the front section toward the forehead of the patient when said legs are in straddling relationship to the nose of the patient, said lip adapted for receipt of a piece of surgical tape to secure the base to the face of the patient.

* * * * *